United States Patent [19]

Wheeler

[11] 4,423,064

[45] Dec. 27, 1983

[54] BIOCIDAL ESTERS OF ALKYNOIC ACIDS

[75] Inventor: Thomas N. Wheeler, Charleston, W. Va.

[73] Assignee: Union Carbide Corporation, Danbury, Conn.

[21] Appl. No.: 278,721

[22] Filed: Jun. 29, 1981

[51] Int. Cl.$^3$ .................... A01N 37/34; A01N 37/06; C07C 69/606; C07C 121/75
[52] U.S. Cl. ............................... 424/304; 260/465 D; 562/429; 562/433; 424/263; 562/434; 562/465; 424/274; 562/598; 424/275; 424/285; 424/305; 424/308; 424/309; 424/314; 546/300; 546/301; 546/330; 546/335; 546/342; 548/513; 549/66; 549/79; 549/499; 560/9; 560/11; 560/19; 560/20; 560/55; 560/121; 560/122; 560/123; 560/124; 560/125; 560/126; 560/128; 560/221; 562/426
[58] Field of Search .................. 260/465 D; 560/221, 560/9, 11, 19, 20, 55, 121–126, 128, 221; 562/426, 429, 433, 434, 465, 598; 546/301, 342; 549/66, 79, 499; 424/263, 274, 275, 285, 304, 305, 314; 548/513

[56] References Cited

U.S. PATENT DOCUMENTS

| | | | |
|---|---|---|---|
| 3,966,244 | 12/1976 | Fujimoto et al. | 260/332.2 A |
| 4,039,680 | 8/1977 | Fujimoto et al. | 424/275 |
| 4,042,710 | 8/1977 | Bull et al. | 424/304 |
| 4,058,622 | 11/1977 | Fujimoto et al. | 424/308 |
| 4,062,968 | 12/1977 | Fujimoto et al. | 424/275 |
| 4,161,536 | 7/1979 | Drabek et al. | 424/304 |
| 4,291,057 | 9/1981 | Wheeler | 424/304 |

FOREIGN PATENT DOCUMENTS 862499 6/1978 Belgium .

Primary Examiner—Dolph H. Torrence
Attorney, Agent, or Firm—G. L. Coon; J. A. Shedden

[57] ABSTRACT

This invention relates to novel ester compounds derived from alkynoic acids and to their preparation. This invention is also directed to insecticidal and miticidal compositions comprising an acceptable carrier and an insecticidally or miticidally effective amount of a novel ester compound of this invention as well as a method of controlling pests by subjecting them to an insecticidally or miticidally effective amount of a novel ester compound of this invention.

27 Claims, No Drawings

BIOCIDAL ESTERS OF ALKYNOIC ACIDS

FIELD OF THE INVENTION

This invention relates to novel ester compounds derived from alkynoic acids which exhibit superior insecticidal and miticidal activity.

BACKGROUND OF THE INVENTION

The development of new agricultural pesticides such as pyrethroids, carbamates and phosphorous compounds is presently an active field of research. A substantial number of researchers in this field endeavor to develop new types of pesticidal compounds for eliminating undesirable pests, combatting a wide variety of pesticide-resistant pests, enhancing the harvested quantity of crops and the like. Various pyrethroidal ester compounds having pesticidal activity have been developed and are disclosed in U.S. Pat. No. 4,161,536, U.S. Pat. No. 4,042,710, U.S. Pat. No. 3,966,244, U.S. Pat. No. 4,039,680, U.S. Pat. No. 4,058,622, U.S. Pat. No. 4,062,968, U.S. Patent Application Ser. No. 054,212, filed July 2, 1979, and Belgium Pat. No. 862,499. As a result of extensive research in the development of new agricultural pesticides, the present invention provides novel pyrethroidal ester compounds derived from alkynoic acids, as structurally depicted below, which have beneficial utility as insecticides and miticides.

SUMMARY OF THE INVENTION

The novel compounds of this invention are esters derived from alkynoic acids which can be depicted structurally as follows:

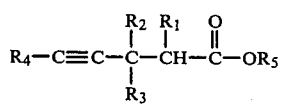

wherein:

$R_1$ is:
- an alkyl or alkenyl group having no more than five carbon atoms, or
- a cycloalkyl or cycloalkenyl group having no more than six carbon atoms;

$R_2$ and $R_3$ are independently:
- hydrogen, or
- an alkyl group having no more than three carbon atoms;

$R_4$ is:
- hydrogen,
- an alkyl or alkenyl group having no more than ten carbon atoms, or
- phenyl or phenyl substituted with alkyl, halogen, cyano, nitro, alkoxy, alkylthio, alkylsulfinyl, alkylsulfonyl or dialkylamino groups; and $R_5$ is:
- a member selected from the group consisting of:

hydrogen, 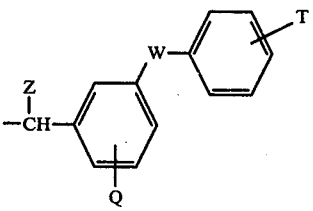

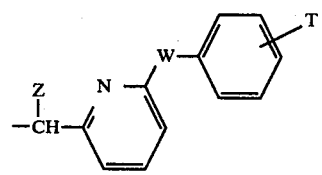

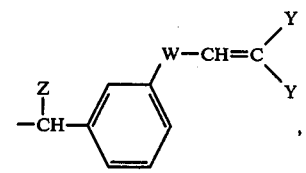

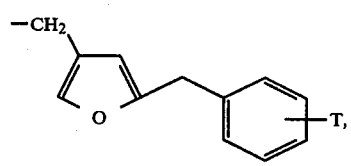

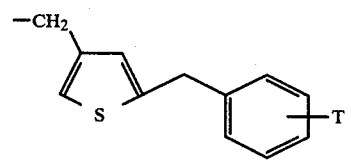

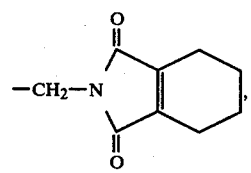

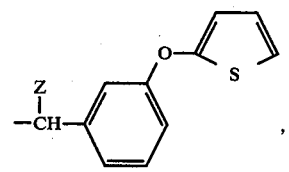

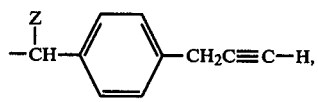

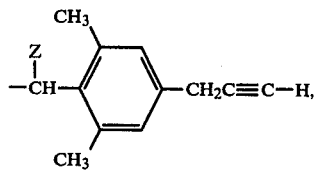

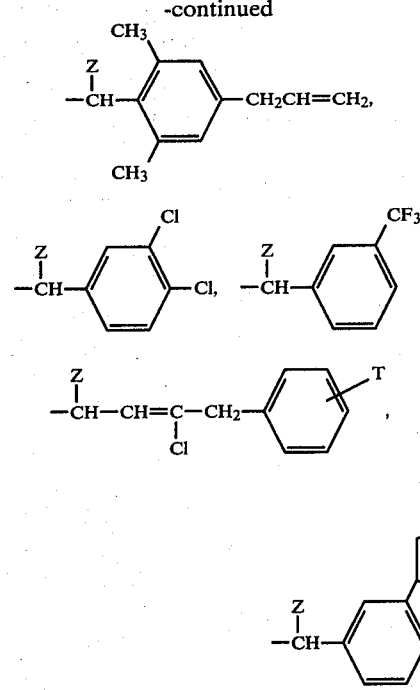

wherein:
Z is:
  hydrogen,
  cyano,
  thioamido,
  an alkyl or haloalkyl group having no more than three carbon atoms,
  a cycloalkyl or cycloalkenyl group having no more than six carbon atoms, or
  an alkenyl, haloalkenyl, or alkynyl group having no more than five carbon atoms;
Q and T are independently:
  hydrogen,
  cyano,
  nitro,
  halogen,
  alkyl,
  haloalkyl,
  alkylthio,
  alkylsulfinyl,
  alkylsulfonyl,
  dialkylamino,
  acylamido,
  alkoxy,
  aryloxy,
  arylthio,
  arylsulfinyl, or
  arylsulfonyl,
  provided that neither Q or T includes more than three aliphatic carbon atoms or more than six aromatic carbon atoms;
W is:
  oxygen,
  sulfur or its oxides, or
  methylene; and
Y is:
  bromine, or
  chlorine.

It is noted that when $R_5$ is hydrogen, novel carboxylic acid compounds are formed which are useful as intermediates in the formation of the novel ester compounds of this invention.

This invention further provides an insecticidal and miticidal composition comprising an acceptable carrier and as the active toxicant an insecticidally or miticidally effective amount of a novel ester compound derived from an alkynoic acid as structurally described above.

This invention also relates to a method of controlling insects and mites which comprises subjecting them to an insecticidally or miticidally effective amount of a novel ester compound derived from an alkynoic acid as structurally described above.

This invention still further relates to methods of preparing the novel ester compounds derived from alkynoic acids as structurally described above.

DESCRIPTION OF PREFERRED EMBODIMENTS

The novel ester compounds derived from alkynoic acids of this invention contain, as an essential characteristic, a carbon-carbon triple bond (C≡C) as structurally depicted above. The novel carboxylic acid intermediate compounds of this invention are those of the above formula in which $R_5$ is hydrogen and $R_1$, $R_2$, $R_3$ and $R_4$ are as described above. The novel ester compounds derived from alkynoic acids of this invention are those of the above formula in which $R_5$ is

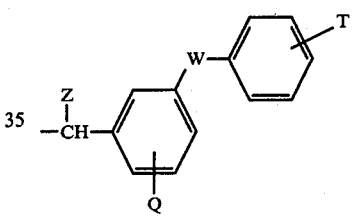

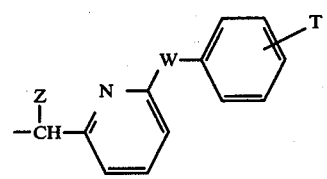

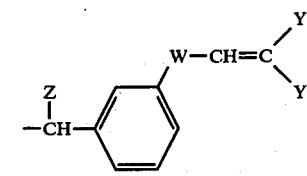

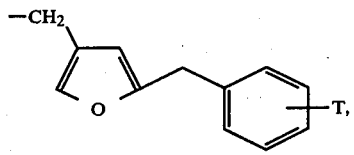

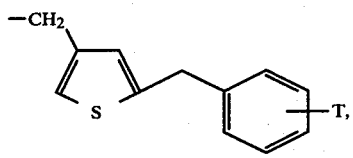

-continued

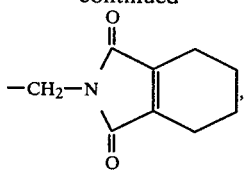

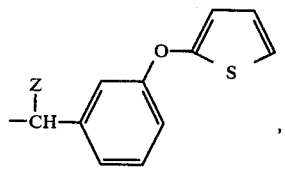

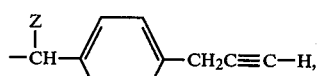

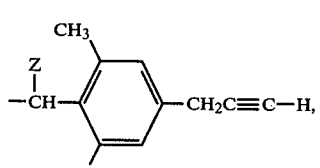

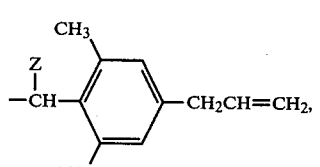

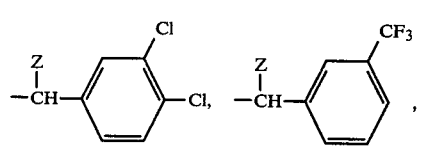

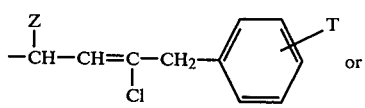

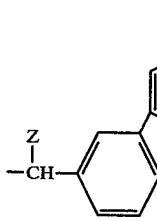

and $R_1$, $R_2$, $R_3$, $R_4$, Z, Q, T, W and Y are as described above. The novel carboxylic acid intermediate compounds are useful in the preparation of the insecticidally and miticidally active novel ester compounds of this invention.

The preferred compounds of this invention are those of the above formula wherein $R_1$ is ethyl, isopropyl or cyclopropyl. Most preferably, $R_1$ is isopropyl. It is preferred that $R_2$ and $R_3$ are both hydrogen. It is most preferred that either $R_2$ or $R_3$ is hydrogen and the other member of this pair is methyl. $R_4$ is preferably hydrogen or an alkyl group having from one to six carbon atoms inclusive. Most preferably, $R_4$ is hydrogen. $R_5$ is preferably hydrogen when the desired product is the novel carboxylic acid compounds of this invention or

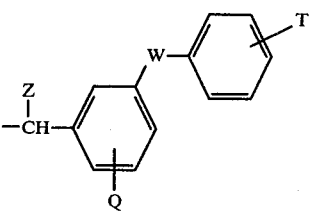

when the desired product is the novel ester compounds derived from alkynoic acids of this invention. When $R_5$ is

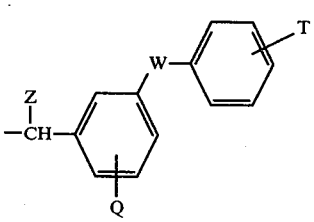

then Z is preferably hydrogen, cyano or a lower alkyl group having from one to three carbon atoms inclusive, most preferably, Z is cyano; Q and T are preferably hydrogen or a lower alkyl group having from one to three carbon atoms inclusive, most preferably, Q and T are hydrogen; and W is preferably oxygen. The most preferred novel carboxylic acid compounds of this invention are 2-isopropyl-4-pentynoic acid and 2-isopropyl-3-methyl-4-pentynoic acid. The most preferred novel ester compounds derived from alkynoic acids of this invention are (α-cyano-m-phenoxybenzyl) 2-isopropyl-4-pentynoate and (α-cyano-m-phenoxybenzyl) 2-isopropyl-3-methyl-4-pentynoate.

Illustrative of the preferred novel carboxylic acids of this invention are as follows:
2,3-dimethyl-4-pentynoic acid
2-ethyl-3-methyl-4-pentynoic acid
2-propyl-3-methyl-4-pentynoic acid
2-cyclopropyl-3-methyl-4-pentynoic acid
2-cyclopropyl-4-pentynoic acid
2-isopropyl-3,3-dimethyl-4-pentynoic acid
2-cyclopropyl-3,3-dimethyl-4-pentynoic acid
2-isopropyl-3-ethyl-4-pentynoic acid
2-isopropyl-3-cyclopropyl-4-pentynoic acid
2-isopropyl-4-hexynoic acid
2-isopropyl-3-methyl-4-hexynoic acid
2-isopropyl-4-heptynoic acid
2-cyclopropyl-3-methyl-4-heptynoic acid
2-isopropyl-3-methyl-4-octynoic acid
2-isopropyl-3-methyl-4-nonynoic acid
2-isopropyl-3-methyl-4-decynoic acid
2-isopropyl-3,6-dimethyl-4-heptynoic acid
2-isopropyl-3-methyl-5-(2-cyclohexenyl)-4-pentynoic acid
2-isopropyl-3-methyl-5-phenyl-4-pentynoic acid
2-isopropyl-3-methyl-5-(4'-chlorophenyl)-4-pentynoic acid
2-cyclopropyl-3-methyl-5-(3',4'-methylenedioxyphenyl)-4-pentynoic acid
2-isopropyl-3-methyl-5-(4'-nitrophenyl)-4-pentynoic acid 2-isopropyl-3-methyl-5-(4'-cyanophenyl)-4-pentynoic acid
2-isopropyl-3-methyl-5-(4'-methoxyphenyl)-4-pentynoic acid
2-phenoxybenzyl-2-isopropyl-3-methyl-5-(4'-methylthiophenyl)-4-pentynoic acid
2-isopropyl-5-(4'-methylsulfinylphenyl)-4-pentynoic acid
2-isopropyl-5-(4'-propylsulfonylphenyl)-4-pentynoic acid
2-isopropyl-3-methyl-5-(4'-dimethylaminophenyl)-4-pentynoic acid
2-isopropyl-3-methyl-5-(4'-methylphenyl)-4-pentynoic acid
2-isopropyl-3-methyl-4-pentynoic acid
2-isopropyl-4-decynoic acid
2-isopropyl-5-(3',4'-methylenedioxyphenyl)-4-pentynoic acid
2-isopropyl-3-methyl-4-pentynoic acid
2-isopropyl-4-pentynoic acid
2-isopropyl-3-methyl-4-pentynoic acid
2-isopropyl-5-(4'-chlorophenyl)-4-pentynoic acid
3-methyl-4-pentynoic acid
4-pentynoic acid
2-isopropyl-3,6,6-trimethyl-4-heptynoic acid Illustrative of the preferred novel ester compounds derived from alkynoic acids of this invention are as follows:

(α-cyano-m-phenoxybenzyl) 2,3-dimethyl-4-pentynoate
(α-cyano-m-phenoxybenzyl) 2-ethyl-3-methyl-4-pentynoate
(α-cyano-m-phenoxybenzyl) 2-propyl-3-methyl-4-pentynoate
(α-cyano-m-phenoxybenzyl) 2-cyclopropyl-3-methyl-4-pentynoate
(α-cyano-m-phenoxybenzyl) 2-cyclopropyl-4-pentynoate
(α-cyano-m-phenoxybenzyl) 2-isopropyl-3,3-dimethyl-4-pentynoate
(α-cyano-m-phenoxybenzyl) 2-cyclopropyl-3,3-dimethyl-4-pentynoate
(α-cyano-m-phenoxybenzyl) 2-isopropyl-3-ethyl-4-pentynoate
(α-cyano-m-phenoxybenzyl) 2-isopropyl-3-cyclopropyl-4-pentynoate
(α-cyano-m-phenoxybenzyl) 2-isopropyl-4-hexynoate
(α-cyano-m-phenoxybenzyl) 2-isopropyl-3-methyl-4-hexynoate
(α-cyano-m-phenoxybenzyl) 2-isopropyl-4-heptynoate
(α-cyano-m-phenoxybenzyl) 2-cyclopropyl-3-methyl-4-heptynoate
(α-cyano-m-phenoxybenzyl) 2-isopropyl-3-methyl-4-octynoate
(α-cyano-m-phenoxybenzyl) 2-isopropyl-3-methyl-4-nonynoate
(α-cyano-m-phenoxybenzyl) 2-isopropyl-3-methyl-4-decynoate
(α-cyano-m-phenoxybenzyl) 2-isopropyl-3,6-dimethyl-4-heptynoate
(α-cyano-m-phenoxybenzyl) 2-isopropyl-3,6,6-trimethyl-4-heptynoate
(α-cyano-m-phenoxybenzyl) 2-isopropyl-3-methyl-5-(2-cyclohexenyl)-4-pentynoate
(α-cyano-m-phenoxybenzyl) 2-isopropyl-3-methyl-5-phenyl-4-pentynoate
(α-cyano-m-phenoxybenzyl) 2-isopropyl-3-methyl-5-(4'-chlorophenyl)-4-pentynoate
(α-cyano-m-phenoxybenzyl) 2-cyclopropyl-3-methyl-5-(3',4'-methylenedioxyphenyl)-4-pentynoate
(α-cyano-m-phenoxybenzyl) 2-isopropyl-3-methyl-5-(4'-nitrophenyl)-4-pentynoate
(α-cyano-m-phenoxybenzyl) 2-isopropyl-3-methyl-5-(4'-cyanophenyl)-4-pentynoate
(α-cyano-m-phenoxybenzyl) 2-isopropyl-3-methyl-5-(4'-methoxyphenyl)-4-pentynoate
(α-cyano-m-phenoxybenzyl) 2-phenoxybenzyl-2-isopropyl-3-methyl-5-(4'-methylthiophenyl)-4-pentynoate
(α-cyano-m-phenoxybenzyl) 2-isopropyl-5-(4'-methylsulfinylphenyl)-4-pentynoate
(α-cyano-m-phenoxybenzyl) 2-isopropyl-5-(4'-propylsulfonylphenyl)-4-pentynoate
(α-cyano-m-phenoxybenzyl) 2-isopropyl-3-methyl-5-(4'-dimethylaminophenyl)-4-pentynoate
(α-cyano-m-phenoxybenzyl) 2-isopropyl-3-methyl-5-(4'-methylphenyl)-4-pentynoate
[3-(2,2-dichlorovihyloxy)-α-cyanobenzyl]2-isopropyl-3-methyl-4-pentynoate
[3-(2,2-dichlorovinyloxy)-α-cyanobenzyl]2-isopropyl-3-methyl-5-(4'-chlorophenyl)-4-pentynoate
(α-ethynyl-m-phenoxybenzyl) 2-isopropyl-3-methyl-4-pentynoate
(α-ethynyl-m-phenoxybenzyl) 2-isopropyl-4-decynoate
(α-ethynyl-m-phenoxybenzyl) 2-isopropyl-5-(3',4'-methylenedioxyphenyl)-4-pentynoate
(α-thioamido-m-phenoxybenzyl) 2-cyclopropyl-3-methyl-4-pentynoate
(α-thioamido-m-phenoxybenzyl) 2-isopropyl-3-methyl-4-pentynoate
(α-thioamido-m-phenoxybenzyl) 2-isopropyl-3-methyl-5-(4'-chlorophenyl)-4-pentynoate
(α-methyl-m-phenoxybenzyl) 2-isopropyl-4-pentynoate
(α-allyl-m-phenoxybenzyl) 2-isopropyl-4-pentynoate
(α-trifluoromethyl-m-phenoxybenzyl) 2-isopropyl-3-methyl-4-pentynoate
[α-cyano-m-(4-fluorophenoxy)benzyl] 2-isopropyl-4-pentynoate
[α-cyano-m-(4-fluorophenoxy)benzyl] 2-isopropyl-3-methyl-4-hexynoate
[α-cyano-3-(4'-fluorophenoxy)-6-fluorobenzyl] 2-isopropyl-4-pentynoate
[α-cyano-3-(4'-fluorophenoxy)-6-fluorobenzyl] 2-isopropyl-3-methyl-4-pentynoate
(5-benzyl-3-furylmethyl) 2-isopropyl-4-pentynoate
(5-benzyl-3-thiophenemethyl) 2-isopropyl-3-methyl-4-pentynoate
(3,4,5,6-tetrahydrophthalimidomethyl) 2-isopropyl-3-methyl-4-pentynoate
[m-(2-thiophenoxy)benzyl] 2-isopropyl-4-pentynoate
(4-propargylbenzyl) 2-isopropyl-3-methyl-4-pentynoate
(α-cyano-m-benzylbenzyl) 2-isopropyl-4-pentynoate
(2,6-dimethyl-4-proparglybenzyl) 2-isopropyl-5-(4'-chlorophenyl)-4-pentynoate
(α-cyano-3,4-dichlorobenzyl) 2-isopropyl-3-methyl-4-pentynoate
(α-cyano-m-trifluoromethyl) 2-isopropyl-5-(4'-chlorophenyl)-4-pentynoate
[3-chloro-4-(p-chlorophenyl)-2-butenyl] 2-isopropyl-3-methyl-4-pentynoate

[α-cyano-6-phenoxy-2-pyridinemethyl] 2-isopropyl-3-methyl-4-pentynoate

[α-cyano-6-phenoxy-2-pyridinemethyl] 2-isopropyl-4-pentynoate

[α-methyl-6-phenoxy-2-pyridinemethyl] 2-isopropyl-3-methyl-4-pentynoate

[α-methyl-6-(4-fluorophenoxy)-2-pyridinemethyl] 3-methyl-4-pentynoate

[α-methyl-6-(4-trifluorophenoxy)-2-pyridinemethyl] 4-pentynoate

The compounds of this invention can be prepared in accordance with a variety of methods. The preferred methods for preparing the novel carboxylic acid compounds of this invention are illustrated by the general reaction schemes (Method I and Method II) set forth below in which $R_1$, $R_2$, $R_3$, and $R_4$ are as described above and R is a lower alkyl group having preferably from one to four carbon atoms inclusive.

METHOD I

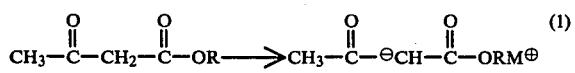
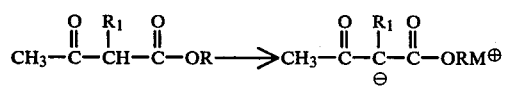
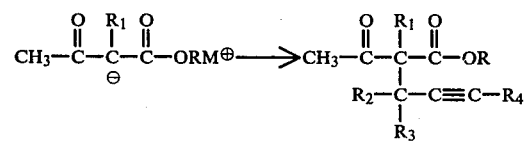
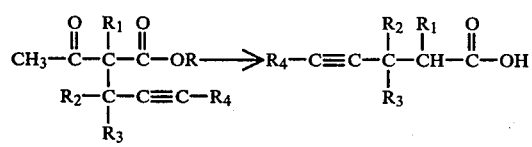

Method I is the well-known acetoacetic ester synthesis of carboxylic acids substituted in the α-position. See H. O. House, *Modern Synthetic Reactions*, 2nd Edition, W. A. Benjamin, Inc., Menlo Park, Calif. 1972, pp. 734–36. Method I works well only in those cases for which $R_2$ and $R_3$ are both hydrogen (e.g., 2-isopropyl-4-pentynoic acid). For those carboxylic acids in which either $R_2$ or $R_3$ is other than hydrogen (e.g., 2-isopropyl-3-methyl-4-pentynoic acid), extensive decomposition and undesirable by-products result if Method I is used.

METHOD II

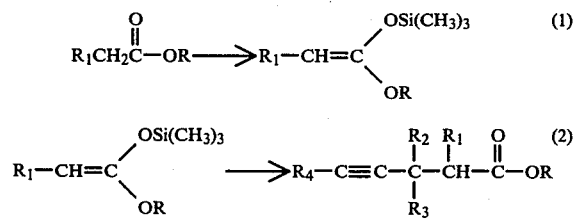

-continued
METHOD II

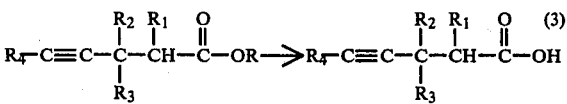

Method II has been reported in the literature as a route of α-tert-butylacetic acid esters. See M. T. Reetz and K. Schwellnus, *Tett. Letters,* pp. 1455–1458, 1978. Step (1) in Method II involves the synthesis of alkyltrimethylsilyl acetate of ketenes. These ketene intermediates are synthesized by treatment of the readily available alkyl acetates with lithium amide bases to form the enolate which is then trapped by reaction with chlorotrimethylsilane. Examples of suitable based which may be used are lithium diethylamide, lithium diisopropylamide (LDA), lithium isopropylcyclohexylamide, lithium bis(trimethylsilyl)amide, and the like. Suitable solvents for step (1) of method II include 1,2-dimethoxyethane, ethyl ester, tetrahydrofuran, benzene, toluene, hexane and other similar organic solvents which do not react with the reagents employed. The preferred solvent for this step is tetrahydrofuran. Step (1) of Method II is preferably conducted in the temperature range of −76° to 0° C. The ketene alkyltrimethylsilyl acetals isolated in step (1) of Method II may be distilled, but they must not be allowed to come in contact with acid or moisture. In step (2) of Method II the ketene alkyltrimethylsilylacetals are alkylated with propargylic halides in the presence of a Lewis acid catalyst. A variety of Lewis acids, e.g., boron trifluoride, aluminum chloride, ferric chloride, antimony pentafluoride, stannic chloride, or zinc chloride, may be used in this alkylation. The Lewis acid is used in catalytic amounts, preferably in the range of 1–5 mol percent. Any organic solvent that is compatible with the reagents may be used in step (2) of Method II. A preferred solvent/catalyst combination for this step is zinc chloride/methylene chloride. Step (2) of Method II is not critically dependent on temperature and may be carried out over a range of temperature from −30° C. to +50° C. and at autogeneous pressures. The reaction is preferably carried out at room temperature (30° C.).

The novel ester compounds derived from alkynoic acids of this invention may be prepared by any of several methods which involve reacting an alcohol of the formula:

$R_5$—OH with an acid of the formula:

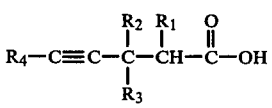

or a reactive derivative thereof. $R_1$, $R_2$, $R_3$, $R_4$ and $R_5$ are as described above and X is halogen in this general method and the methods shown below. The term reactive derivative of the acid refers to an acid halide, an acid anhydride, an ester with an alcohol having a low boiling point, an alkali metal salt, a silver salt, or an organic tertiary amine base salt of the acid. In certain instances, the halide or sulfoxylate derived from the alcohol $R_5$—OH may be reacted with the acid derivative. These methods are illustrated by the general reaction schemes (Methods III through VIII) set forth below:

METHOD III

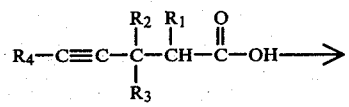

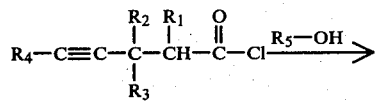

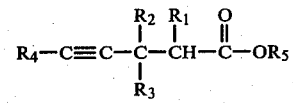

The acid halide is obtained by reacting the carboxylic acid with thionyl chloride, phosphorous trichloride or the like. The desired ester can be obtained in high yield by reacting the alcohol and the acid halide at room temperature using a proton acceptor; for example, an organic tertiary amine such as pyridine, triethylamine, and the like. The acid halides may be acid fluorides, bromides, or chlorides, but an acid chloride is generally preferred. The presence of an inert solvent in the esterification reaction is not essential, but it is generally preferred to use an inert solvent to assure a smooth reaction in this step. Any solvent may be used which is inert to the reactants and the ester product. Preferred solvents include benzene, toluene, carbon tetrachloride, methylene chloride, chloroform, and the like. An acid anhydride may optionally be used in place of the acid halide in Method III.

METHOD IV

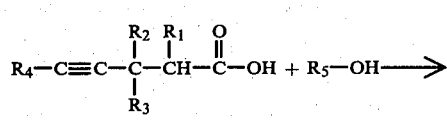

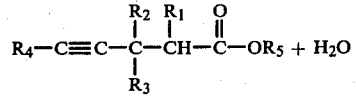

The novel ester compounds derived from alkynoic acids of this invention may be prepared by reacting the carboxylic acids with the alcohols in an appropriate inert solvent at room temperature or an elevated temperature under an appropriate dehydrating condition, e.g., dicyclohexylcarbodiimide. Suitable solvents for this method are ether, toluene, benzene, carbon tetrachloride, methylene chloride, hexane, and the like.

METHOD V

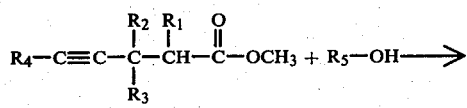

METHOD V —continued

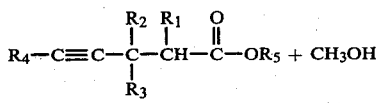

When the alcohol $R_5$—OH is stable to strong base, the desired esters may be obtained by refluxing a low boiling point alcohol ester of the acid in the presence of an appropriate organic base catalyst in an inert solvent while removing the low boiling alcohol liberated in the reaction by azeotropic distillation. The base should be the alkali metal alkoxide corresponding to the low boiling alcohol of the ester used or an alkali metal hydride, e.g. sodium or lithium hydride. Preferred solvents for this reaction are toluene or benzene.

METHOD VI

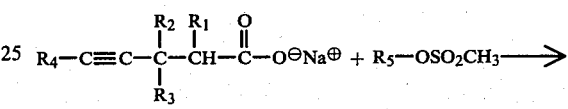

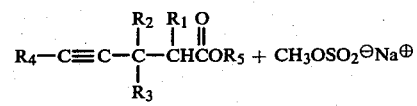

METHOD VII

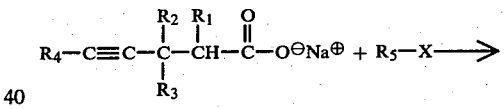

When a halide or sulfoxylate of the alcohol $R_5$—OH is used, the carboxylic acid is generally employed in the form of an alkali metal salt, a silver salt, or an organic tertiary amine base salt. These salts may be formed in situ by adding simultaneously the carboxylic acid and the corresponding base to the reaction system. In this case, a solvent such as toluene, benzene, acetone, dimethylsulfoxide, dimethylformamide, and the like is preferred, and the reaction is preferably conducted by heating the reaction mixture at or below the boiling point of the solvent used. Methods VI and VII above are illustrative of processes using a halide or sulfoxylate of the alcohol $R_5$—OH.

METHOD VIII

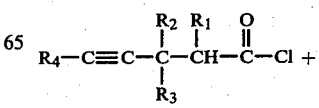

-continued
METHOD VIII

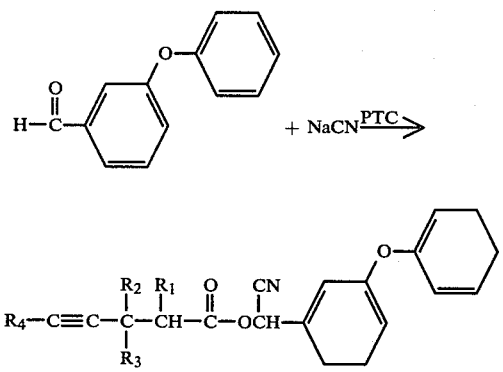

An especially active series of novel ester compounds are those prepared from α-cyano-m-phenoxybenzyl alcohol. These novel ester compounds can be conveniently prepared as shown in Method VIII. The process illustrated in Method VIII utilizes from 1.0 to 1.1 molar equivalents of m-phenoxybenzaldehyde, 1.0 molar equivalents of the acid chloride, and 1.1 to 1.5 molar equivalents of sodium cyanide. The phase transfer catalyst (PTC) is employed in 0.01–0.10 molar equivalent amounts. In general, larger quantities of the phase transfer catalyst (PTC) result in shorter reaction times. Suitable phase transfer catalysts for Method VIII are methyltricaprylammonium chloride, benzyltriethylammonium chloride, hexadecyltributylphosphonium bromide, tetra-n-butylammonium hydrogen sulfate, tetra-n-butylammonium chloride, trioctylpropylammonium chloride, and the like. Method VIII is neither temperature nor pressure sensitive and may be run over a wide range of these variables. A preferred reaction condition is room temperature and autogeneous pressure. The alcohols used to prepare the novel ester compounds of this invention are all known compounds whose preparation is described in the chemical literature. See M. Elliott, *Synthetic Pyrethroids*, ACS Symposium Series 42, American Chemical Society, Washington, D.C., 1977.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attachment by insects and mites upon plants or other material to which the pesticides are applied. With respect to plants, they have a high mrgin of safety in than when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are compatible with other constituents of the spray schedule, and they may be used in the soil, upon the seeds, or the roots of plants without injuring either the seeds or roots of plants. Mixtures of the active compounds may be employed if desired as well as combinations of the active compounds of this invention with one or more fungicides, bactericides, acaricides, nematocides, insecticides or other biologically active compounds.

The following examples are illustrative of the present invention and are not intended as a limitation upon the scope thereof.

EXAMPLE I

Part A: Preparation of Ethyl
2-Propargyl-2-Isopropylacetoacetate

A 1 liter flask was equipped with a mechanical stirrer, addition funnel, reflux condenser and nitrogen inlet. The flask was dried with external heat and then charged with 12.00 grams (0.25 mol) of 50% sodium hydride dispersed in mineral oil. The mineral oil was removed by two 50 milliliter washings with toluene and then 200 milliliters of toluene was added to the flask. 43.06 grams (0.25 mol) of ethyl 2-isopropylacetoacetate was added dropwise to the flask along with three drops of dry ethanol. Hydrogen was virorously evolved and the reaction temperature rose to 65° C. When all the ethyl 2-isopropylacetoacetate had been added, the reaction mixture was heated to 75° C. for one hour and then cooled to 10° C. with an ice bath. The reaction mixture at this point was thick and light green in color. 37.18 grams (0.25 mol) of propargyl bromide was then added dropwise and the reaction mixture was allowed to stir overnight at room temperature. After one hour of stirring, the reaction mixture had thinned and turned a rust color. Following the overnight stirring period, the reaction mixture was heated to 85° C. for two hours and then cooled to room temperature. The reaction mixture was cautiously quenched with 10 milliliters of ice water followed by the addition of 250 milliliters of ice water and the resulting layers were separated. The toluene was washed three times with water, dried (MgSO$_4$) and removed under vacuum to leave a red oil. The red oil was vacuum distilled through a vigreux still to give 33.5 grams (0.16 mol) of ethyl 2-propargyl-2-isopropylacetoacetate having a boiling point of 61°–68° C. at 0.20 millimeters pressure.

NMR (CDCl$_3$,δ): 0.95 (6H, pair of d); 1.24 (3H,t); 2.0 (t, 1H); 2.20 (s,3H); 2.52 (m, 1H); 2.70 (d, 2H); 4.21 (q, 2H).

IR (neat, cm$^{-1}$): 3290 (s), 2970 (s), 2940 (m), 2870 (m), 2130 (w), 1710 (s), 1620 (w), 1460 (m), 1390 (m), 1370 (m), 1355 (m), 1265 (s), 1225 (s), 1180 (s), 1130 (m), 1060 (m), 1020 (m), 860 (w).

Part B: Preparation of 2-Isopropyl-4-Pentynoic Acid

A 1 liter flask was equipped with a mechanical stirrer, addition funnel, reflux condenser and nitrogen inlet. 33.52 grams (0.169 mol) of ethyl 2-propargyl-2-isopropylacetoacetate prepared in Part A and 350 milliliters of 15% potassium hydroxide-ethanol were added into the flask and refluxed overnight under nitrogen. Following the overnight refluxing, most of the ethanol was removed under vacuum and the remaining material was taken up in three volumes of water. This remaining material was extracted three times with 150 milliliters of ether. The formed aqueous layer was acidified with 3 N HCl and the resulting oil was extracted into ether. The ether was dried (MgSO$_4$) and removed under vacuum to leave 19.63 grams of a red oil. The red oil was vacuum distilled through a vigreux still to give 13.25 grams (0.095 mol) of 2-isopropyl-4-pentynoic acid.

NMR (CDCl$_3$,δ): 1.00 (d,6H); 1.3–2.3 (m,3H); 2.47 (m,2H); 12.12 (s, 1H).

IR (neat, cm$^{-1}$): 3300 (m), 2960 (s), 2940 (m), 2800–2500 (m), 2130 (w), 1700 (s), 1460 (m), 1415 (m), 1280 (m), 1260 (m), 1200 (m), 930 (m), 640 (m).

EXAMPLE II

Preparation of (α-Cyano-M-Phenoxybenzyl) 2-Isopropyl-4-Pentynoate

A 1 liter flask was equipped with a mechanical stirrer, addition funnel, reflux condenser and nitrogen inlet. A solution of 5.00 grams (0.036 mol) of 2-isopropyl-4-pentynoic prepared in Example I in 25 milliliters of carbon tetrachloride was treated with 2 drops of pyridine and then cooled in an ice bath while stirring under nitrogen. To this solution was added 8.49 grams (0.071 mol) of thionyl chloride. After 5 minutes the ice bath was removed and the reaction mixture was brought to reflux. The reaction mixture was refluxed for 30 minutes, allowed to cool and the carbon tetrachloride was removed under vacuum to leave a red oil. The red oil was taken up in 25 milliliters of carbon tetrachloride and cooled under nitrogen in an ice bath with continuous stirring. To this reaction mixture was added a solution of 8.93 grams (0.036 mol) of α-cyano-m-phenoxybenzyl alcohol, 4.24 grams (0.054 mol) of pyridine and 20 milliliters of carbon tetrachloride. After stirring overnight the reaction mixture was taken up in 150 milliliters of methylene chloride, washed three times with 100 milliliters of 5% HCl, twice with water, dried (MgSO$_4$), and the solvent removed to leave 11.1 grams of a pale yellow oil. The pale yellow oil was purified by chromatography through silica gel to give 4.92 grams (0.01 mol) of (α-cyano-m-phenoxybenzyl) 2-isopropyl-4-pentynoate as a clear, colorless oil. Thin Layer Chromatography (80:20 hexane-ethyl acetate) on silica gel showed one spot at Rf 0.48.

Calculated (weight percent): C, 76.06; H, 6.09; N, 4.03. Found (weight percent): C, 76.32; H, 5.89; N, 3.99.

EXAMPLE III

Part A: Preparation of 1-Trimethylsilyloxy-1-Ethoxy-3-Methylbutene

A 2 liter flask was equipped with a mechanical stirrer, addition funnel, reflux condenser, nitrogen inlet and thermometer. The flask was dried with external heat and then charged with 563 milliliters of dry tetrahydrofuran, 75.9 grams (0.75 mol) of diisopropylamine and cooled to 0° C. Over a 30 minute period 523 milliliters of 1.6 M n-butyl lithium (0.94 mol) was added dropwise. The reaction mixture was stirred at 0° C. for 15 minutes, then cooled to −76° C. in a dry ice-acetone bath and 97.65 grams (0.75 mol) of ethyl isovalerate was added dropwise over about 30 minutes. When this addition was complete, the reaction mixture was stirred for 15 minutes at −76° C., then 205 milliliters (2.20 mol) of chlorotrimethylsilane was added dropwise. When this addition was complete, the dry ice-acetone bath was removed and the reaction mixture allowed to come to room temperature. The reaction mixture was then filtered and concentrated under reduced pressure to give a residue which was triturated with ether and filtered. The filtrate was concentrated under vacuum to give a residue and the residue was vacuum distilled through a vigreux column to give 136.44 grams (1.48 mol) of 1-trimethylsilyloxy-1-ethoxy-3-methylbutene having a boiling point of 78°–88° C. at 30 millimeters pressure.

NMR (CDCl$_3$,δ): 0.22 (s, 9H); 0.95 (d, 6H); 1.21 (t, 3H); 2.50 (m, 1H); 3.76 (m, 2H).

Part B: Preparation of Ethyl 2-Isopropyl-3-methyl-4-Pentynoate

A 250 milliliter flask was equipped with a magnetic stirrer, reflux condenser and nitrogen inlet. The flask was dried with external heat and then charged with 19.92 grams (0.22 mol) of 3-chloro-1-butyne, 30.49 grams (0.15 mol) of 1-trimethylsilyloxy-1-ethoxy-3-methylbutene prepared in Part A, 100 milliliters of dry methylene chloride, and 0.5 grams of anhydrous zinc chloride. The reaction mixture was stirred at room temperature and monitored by infrared for 48 hours. The disappearance of the ketene acetal C═C peak at 1675 cm$^{-1}$ and the appearance of an ester C═O peak at 1720 cm$^{-1}$ was observed. The reaction mixture was then worked up by diluting with 150 milliliters of methylene chloride and washing five times with 100 milliliters of 5% sodium bicarbonate and twice with water. The methylene chloride was dried (MgSO$_4$) and removed under vacuum to give a residue. The residue was vacuum distilled through a vigreux column to give 8.44 grams (0.05 mol) of ethyl 2-isopropyl-3-methyl-4-pentynoate having the appearance of a colorless oil and a boiling point of 66°–76° C. at 7 millimeters pressure.

NMR (CDCl$_3$,δ): 0.8–1.25 (m, 9H); 1.31 (t, 3H); 2.0–2.6 (m, 3H); 2.6–3.2 (m, 1H); 4.2 (q, 2H).

IR (neat, cm$^{-1}$): 3230 (m); 2920 (s); 1730 (s); 1460 (m); 1370 (m); 1300 (m); 1250 (m); 1200 (m); 1170 (s); 1070 (m).

Part C: Preparation of 2-Isopropyl-3-Methyl-4-Pentynoic Acid

A 250 milliliter flask was equipped with a magnetic stirrer, reflux condenser and nitrogen inlet. Into the flask was added 8.44 grams (0.05 mol) of ethyl 2-isopropyl-3-methyl-4-pentynoate prepared in Part B, 5.56 grams (0.14 mol) of sodium hydroxide, 20 milliliters of ethanol and 20 milliliters of water. Following three days of continuous refluxing and stirring under nitrogen, the reaction mixture was cooled to room temperature, diluted with three times its volume of water and extracted twice with ether. Ice was added to the aqueous phase and it was acidified with 3 N HCl, then extracted three times with ether. The ether was washed twice with water, dried (MgSO$_4$) and removed under vacuum to give 5.87 grams (0.04 mol) of 2-isopropyl-3-methyl-4-pentynoic acid having the appearance of a light yellow oil.

NMR (CDCl$_3$,δ): 0.8–1.50 (m, 9H); 1.5–2.1 (m, 1H); 2.1–3.2 (m, 3H); 10.7 (s broad, 1H).

IR (neat, cm$^{-1}$): 3200 (s); 2850 (s); 2260–2700 (m); 1700 (s); 1455 (m); 1420 (m); 1380 (m); 1370 (m); 1270 (m); 1250 (m); 938 (m).

EXAMPLE IV

Preparation of (α-Cyano-M-Phenoxybenzyl) 2-Isopropyl-3-Methyl-4-Pentynoate

A 1 liter flask was equipped with a mechanical stirrer, addition funnel, reflux condenser and nitrogen inlet. A solution of 5.87 grams (0.04 mol) of 2-isopropyl-3-methyl-4-pentynoic acid prepared in Exaple III in 25 milliliters of carbon tetrachloride was treated with 2 drops of pyridine and then cooled in an ice bath while stirring under nitrogen. To this solution was added 9.04 grams (0.08 mol) of thionyl chloride. After 5 minutes the ice bath was removed and the reaction mixture was brought to reflux. The reaction mixture was refluxed for 30 minutes, allowed to cool and the carbon tetrachloride was removed under vacuum to leave a red oil. The red oil was taken up in 25 milliliters of carbon tetrachloride and cooled under nitrogen in an ice bath with continuous stirring. To this reaction mixture was added a solution of 9.02 grams (0.04 mol) of α-cyano-m-phenoxybenzyl alcohol, 6.01 grams (0.76 mol) of pyridine and 20 milliliters of carbon tetrachloride. After stirring overnight the reaction was taken up in 150 milliliters of methylene chloride, washed three times with 100 milliliters of 5% HCl, twice with water, dried (MgSO$_4$) and the solvent removed to leave 10.41 grams of a pale yellow oil. The pale yellow oil was purified by two successive chromatographics through silica gel to give 2.57 grams (0.01 mol) of (α-cyano-m-phenoxybenzyl) 2-isopropyl-3-methyl-4-pentynoate as a clear, colorless oil. Thin Layer Chromatography (80:20 hexaneethyl acetate) on silica gel showed one spot at Rf 0.43.

Calculated (weight percent): C, 76.43; H, 6.41; N, 3.87. Found (weight percent): C, 76.71; H, 6.36; N, 3.52.

EXAMPLES V and VI

Selected novel compounds of this invention were evaluated with respect to their activity against mites and representative insects including an aphid, a caterpillar, a beetle and a fly.

Suspensions of the test compounds were prepared by dissolving one gram of compound in 50 milliliters of acetone in which has been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of test compound. The test concentrations in parts per million by weight (ppm) employed in the tests described hereinbelow were obtained by appropriate dilutions of the stock suspension with water. The test procedures were as follows:

Bean Aphid Foliage Spray Test

Adults and nymphal stages of the bean aphid (Aphis fabae Scop.) reared on potted dwarf nasturtium plants at 68°–70° F. and 50±5 percent relative humidity, constituted the test insects. For testing purposes, the number of aphids per pot were standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application which lasted 25 seconds, weas sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°–70° C. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania*, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of $80\pm5°$ F. and $50\pm5$ percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of $80\pm5°$ F., for three days. Although the larvae could easily consume the leaf within 24 to 48 hours, no more food was added. Larvae which were unable to move the length of the body, even upon stimulation, were considered dead. Percent mortality was recorded for various concentration levels.

Fly Bait Test

Four to six day old adult house flies (*Musca domestica*, L.), reared according to the specifications of the Chemical Specialities Manufacturing Association (Blue Book, McNair-Dorland Co., New York 1954; pages 243–244, 261) under controlled conditions of $80\pm5°$ F. and $50\pm5$ percent relative humidity, were the test insects. The flies were immobilized by anesthetizing with carbon dioxide and twenty-five immobilized individuals, males and females, were transferred to a cage consisting of a standard food strainer about five inches in diameter which was inverted over a wrapping-paper covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty-four hours, at a temperature of $80\pm5°$ F. and the relative humidity of $50\pm5$ percent. Flies which showed no sign of movement on prodding were considered dead. Percent mortality was recorded for various concentration levels.

Mite Foliage Spray Test

Adults and nymphal stage of the two-spotted mite (*Tetraanychus urticae* Koch), reared on Tendergreen bean plants at $80\pm5$ percent relative humidity were the test organisms. Infested leaves from a stock culture were placed on the primary leaves of two bean plants six to eight inches in height, growing in a two-and-a-half inch clay pot. 150–200 Mites, a sufficient number for testing, were transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at $80\pm5$ percent relative humidity for six days, after which a mortality count of motile forms was made. Microscopic examination for motile forms was made on the leaves of the test plants. Any individual which was capable of locomotion upon prodding was considered living. Percent mortality was recorded for various concentration levels.

The results of these tests are set forth in Table A below. In these tests the pesticidal activity of the compounds at the indicated dosage rate against aphid, Southern Armyworm, Bean Beetle, housefly and mite was rated as follows:

A = complete kill at 500 ppm
B = partial kill at 500 ppm
C = no kill at 500 ppm

It should be understood that the insects and mites evaluated are representative of a wider variety of pest which can be controlled by the compounds of this invention.

TABLE A

PESTICIDAL ACTIVITY OF ESTERS OF ALKYNOIC ACIDS

| Example | Compound | Structure | Bean Aphid | Southern Armyworm | Mexican Bean Beetle | Housefly | Mite |
|---|---|---|---|---|---|---|---|
| V | (α-Cyano-m-phenoxybenzyl) 2-isopropyl-4-pentynoate | $H-C\equiv C-CH_2CH(CH(CH_3)_2)CO_2CH(CN)(C_6H_4-O-C_6H_5)$ | A | A | A | A | A |

TABLE A-continued
PESTICIDAL ACTIVITY OF ESTERS OF ALKYNOIC ACIDS

| Example | Compound | Structure | Bean Aphid | Southern Armyworm | Mexican Bean Beetle | Housefly | Mite |
|---|---|---|---|---|---|---|---|
| VI | (α-Cyano-m-phenoxybenzyl) 2-isopropyl-3-methyl-4-pentynoate | $H-C\equiv C-CH(CH_3)-CH(CH(CH_3)_2)-CO_2CH(CN)-C_6H_4-O-C_6H_5$ | A | A | A | A | A |

The results of Table A clearly demonstrate that selected compounds within the scope of this invention possess desirable broad spectrum pesticidal activity against mites and a variety of insects including an aphid, a caterpillar, a beetle and a fly.

What is claimed is:

1. A compound of the formula:

$$R_4-C\equiv C-\underset{R_3}{\overset{R_2}{C}}-\underset{}{\overset{R_1}{CH}}-\overset{O}{\underset{}{C}}-OR_5$$

wherein:

R$_1$ is:
  an alkyl or alkenyl group having no more than five carbon atoms, or
  a cycloalkyl or cycloalkenyl group having no more than six carbon atoms;

R$_2$ and R$_3$ are independently:
  hydrogen, or
  an alkyl group having no more than three carbon atoms;

R$_4$ is:
  hydrogen,
  an alkyl or alkenyl group having no more than ten carbon atoms, or
  phenyl or phenyl substituted with alkyl, halogen, cyano, nitro, alkoxy, alkylthio, alkylsulfinyl, alkylsulfonyl or dialkylamino groups; and R$_5$ is:
  hydrogen, or
  a member selected from the group consisting of:

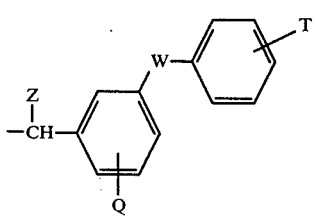

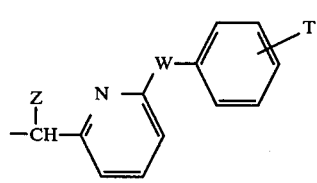

-continued

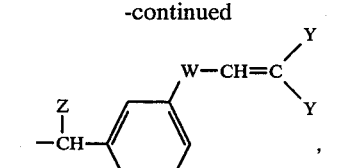

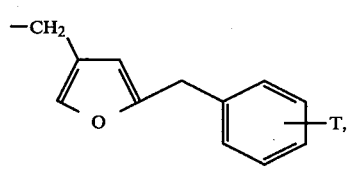

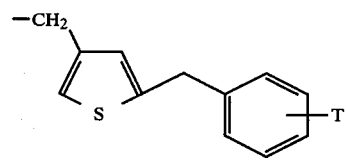

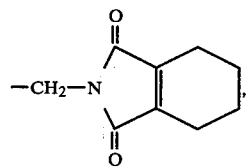

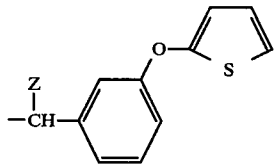

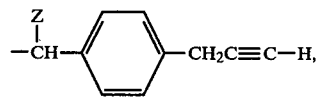

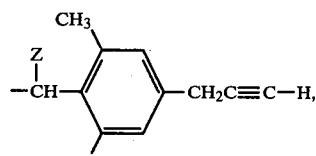

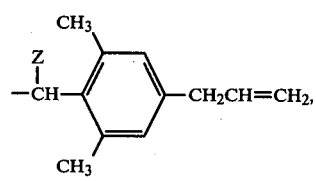

-continued

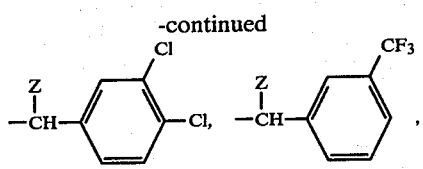

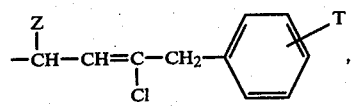

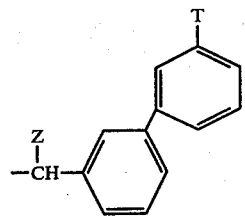

wherein:
Z is:
  hydrogen,
  cyano,
  thioamido,
  an alkyl or haloalkyl group having no more than three carbon atoms,
  a cycloalkyl or cycloalkenyl group having no more than six carbon atoms, or
  an alkenyl, haloalkenyl, or alkynyl group having no more than five carbon atoms;
Q and T are independently:
  hydrogen,
  cyano,
  nitro,
  halogen,
  alkyl,
  haloalkyl,
  alkylthio,
  alkylsulfinyl,
  alkylsulfonyl,
  dialkylamino,
  acylamido,
  alkoxy,
  aryloxy,
  arylthio,
  arylsulfinyl, or
  arylsulfonyl,
  provided that neither Q or T includes more than three aliphatic carbon atoms or more than six aromatic carbon atoms;
W is:
  oxygen,
  sulfur or its oxides, or
  methylene; and
Y is:
  bromine, or
  chlorine.

2. A compound as defined in claim 1 wherein $R_1$ is ethyl, isopropyl or cyclopropyl.

3. A compound as defined in claim 2 wherein $R_2$ and $R_3$ are hydrogen or when either $R_2$ or $R_3$ is hydrogen then the other member of this pair is methyl.

4. A compound of the formula:

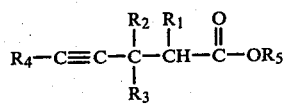

wherein:
  $R_1$ is: ethyl, isopropyl or cyclopropyl;
  $R_2$ and $R_3$ are hydrogen or when either $R_2$ or $R_3$ is hydrogen then the other member of this pair is methyl;
  $R_4$ is:
    hydrogen and
  $R_5$ is:
    a member selected from the group consisting of:

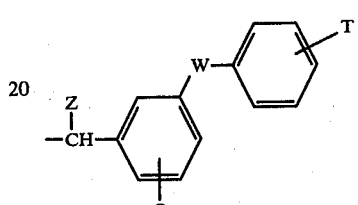

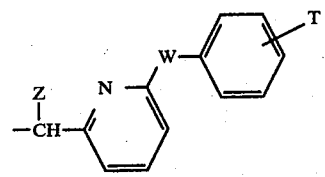

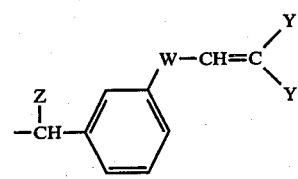

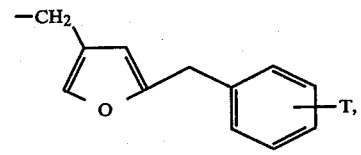

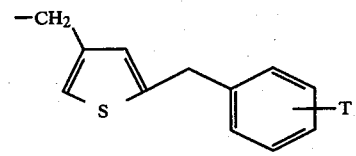

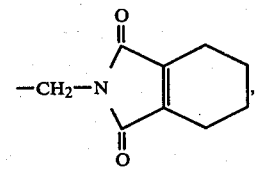

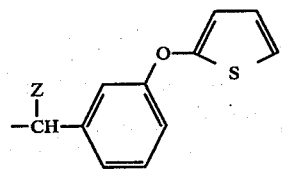

-continued

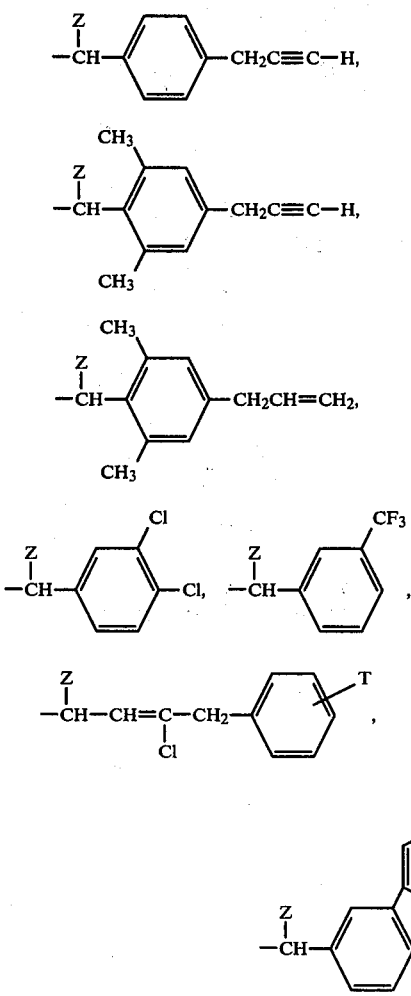

wherein:
Z is:
  hydrogen,
  cyano,
  thioamido,
  an alkyl or haloalkyl group having no more than three carbon atoms,
  a cycloalkyl or cycloalkenyl group having no more than six carbon atoms, or
  an alkenyl, haloalkenyl, or alkynyl group having no more than five carbon atoms;
Q and T are independently:
  hydrogen,
  cyano,
  nitro,
  halogen,
  alkyl,
  haloalkyl,
  alkylthio,
  alkylsulfinyl,
  alkylsulfonyl,
  dialkylamino,
  acylamido,
  alkoxy,
  aryloxy,
  arylthio,
  arylsulfinyl, or
  arylsulfonyl,
  provided that neither Q or T includes more than three aliphatic carbon atoms or more than six aromatic carbon atoms;
W is:
  oxygen,
  sulfur or its oxides, or
  methylene; and
Y is:
  bromine, or
  chlorine.

5. A compound as defined in claim 4 wherein $R_5$ is hydrogen or

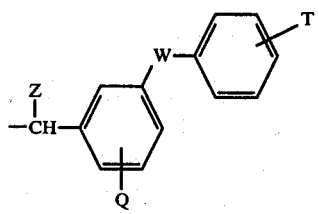

wherein:
Z is cyano,
Q and T are hydrogen, and
W is oxygen.

6. A compound of the formula:

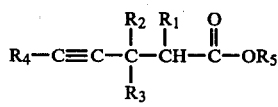

wherein:
$R_1$ is ethyl, isopropyl or cyclopropyl,
$R_2$ and $R_3$ are independently hydrogen or methyl,
$R_4$ is hydrogen, and
$R_5$ is hydrogen.

7. A compound of the formula:

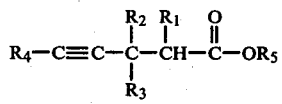

wherein:
$R_1$ is ethyl, isopropyl or cyclopropyl,
$R_2$ and $R_3$ are independently hydrogen or methyl,
$R_4$ is hydrogen, and
$R_5$ is

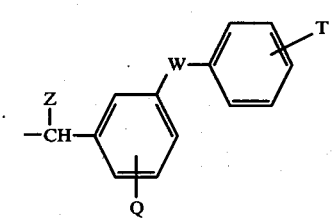

wherein:
Z is cyano,
Q and T are hydrogen, and
W is oxygen.

8. (α-Cyano-m-phenoxybenzyl) 2-isopropyl-4-pentynoate.

9. (α-Cyano-m-phenoxybenzyl) 2-isopropyl-3-methyl-4-pentynoate.

10. 2-Isopropyl-4-pentynoic acid.

11. 2-Isopropyl-3-methyl-4-pentynoic acid.

12. An insecticidal and miticidal composition comprising an acceptable carrier and as the active toxicant an insecticidally or miticidally effective amount of a compound of the formula:

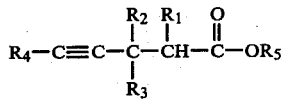

wherein:

R₁ is:
an alkyl or alkenyl group having no more than five carbon atoms, or
a cycloalkyl or cycloalkenyl group having no more than six carbon atoms;

R₂ and R₃ are independently:
hydrogen, or
an alkyl group having no more than three carbon atoms;

R₄ is:
hydrogen,
an alkyl or alkenyl group having no more than ten carbon atoms, or
phenyl or phenyl substituted with alkyl, halogen, cyano, nitro, alkoxy, alkylthio, alkylsulfinyl, alkylsulfonyl or dialkylamino groups; and R₅ is a member selected from the group consisting of:

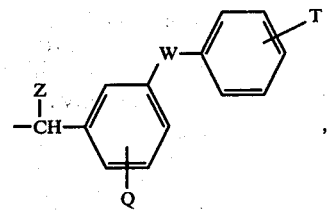

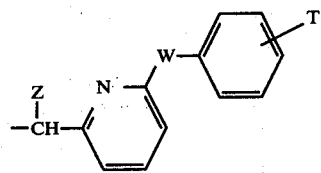

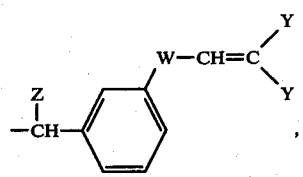

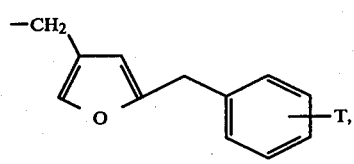

-continued

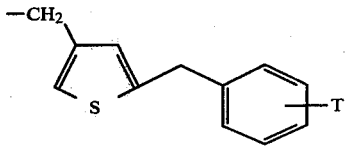

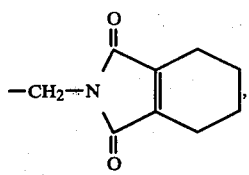

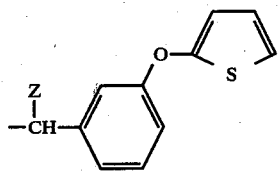

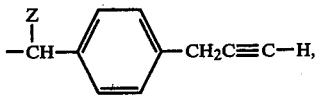

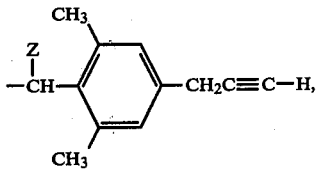

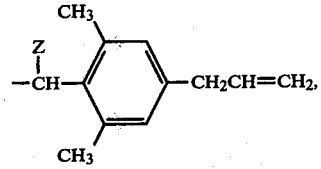

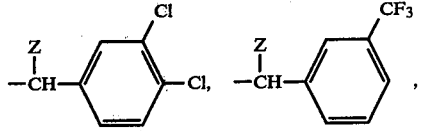

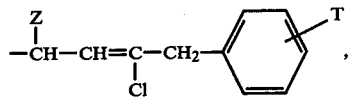

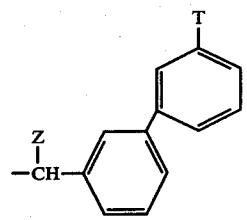

wherein:
Z is:
hydrogen,
cyano,
thioamido, an alkyl or haloalkyl group having no more than three carbon atoms,
a cycloalkyl or cycloalkenyl group having no more than six carbon atoms, or
an alkenyl, haloalkenyl, or alkynyl group having no more than five carbon atoms;

Q and T are independently:
 hydrogen,
 cyano,
 nitro,
 halogen
 alkyl,
 haloalkyl,
 alkylthio,
 alkylsulfinyl,
 alkylsulfonyl,
 dialkylamino,
 acylamido,
 alkoxy,
 aryloxy,
 arylthio,
 arylsulfinyl, or
 arylsulfonyl,
 provided that neither Q or T includes more than three aliphatic carbon atoms or more than six aromatic carbon atoms;

W is:
 oxygen,
 sulfur or its oxides, or
 methylene; and

Y is:
 bromine or
 chlorine.

13. A composition according to claim 12 wherein $R_1$ is ethyl, isopropyl or cyclopropyl.

14. A composition according to claim 13 wherein $R_2$ and $R_3$ are hydrogen or when either $R_2$ or $R_3$ is hydrogen then the other member of this pair is methyl.

15. An insecticidal and miticidal composition comprising an acceptable carrier and as an active toxicant an insecticidally or miticidally effective amount of a compound of the formula:

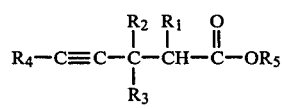

wherein:
 $R_1$ is: ethyl, isopropyl or cyclopropyl;
 $R_2$ and $R_3$ are hydrogen or when either $R_2$ or $R_3$ is hydrogen then the other member of this pair is methyl;
 $R_4$ is:
  hydrogen, and
 $R_5$ is a member selected from the group consisting of:

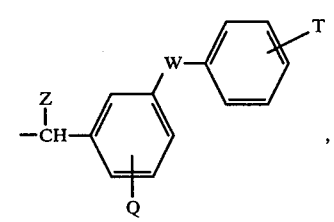

-continued

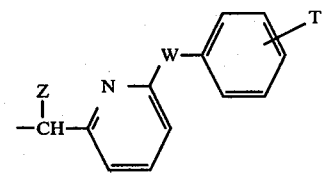

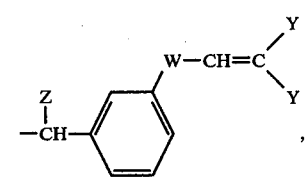

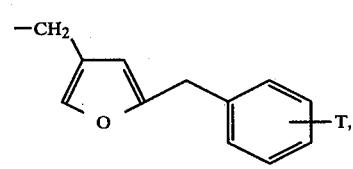

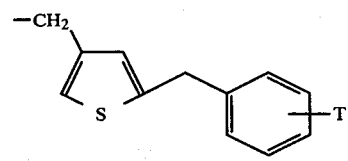

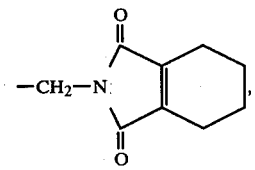

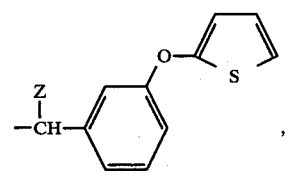

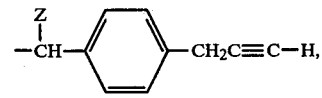

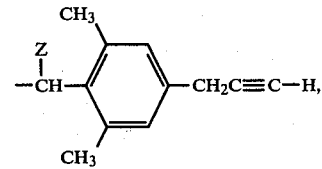

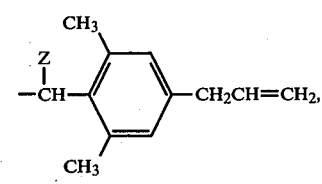

-continued

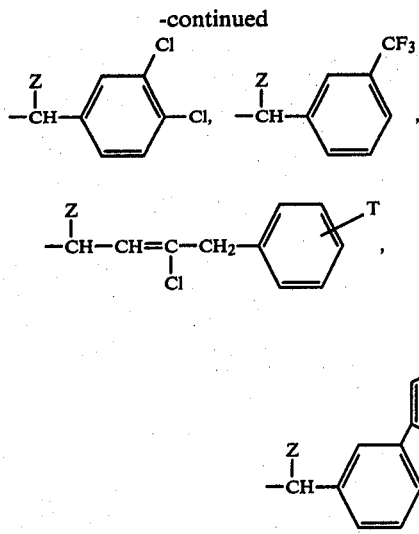

wherein:
Z is:
  hydrogen,
  cyano,
  thioamido
  an alkyl or haloalkyl group having no more than three carbon atoms,
  a cycloalkyl or cycloalkenyl group having no more than six carbon atoms, or an alkenyl, haloalkenyl, or alkynyl group having no more than five carbona toms:
Q and T are independently:
  hydrogen,
  cyano,
  nitro,
  halogen,
  alkyl,
  haloalkyl,
  alkylthio,
  alkylsulfinyl,
  alkylsulfonyl,
  dialkylamino,
  acylamido,
  alkoxy,
  aryloxy,
  arylthio,
  arylsulfinyl, or
  arylsulfonyl,
  provided that neither Q or T includes more than three aliphatic carbon atoms or more than six aromatic carbon atoms;
W is:
  oxygen,
  sulfur or its oxides, or
  methylene; and
Y is:
  bromine or
  chlorine.

16. A composition according to claim 15 wherein $R_5$ is

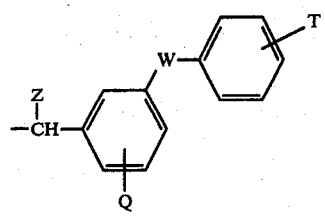

wherein:
Z is cyano,
Q and T are hydrogen, and
W is oxygen.

17. A composition according to claim 15 wherein the active toxicant is (α-cyano-m-phenoxybenzyl) 2-isopropyl-4-pentynoate.

18. A composition according to claim 15 wherein the active toxicant is (α-cyano-m-phenoxybenzyl) 2-isopropyl-3-methyl-4-pentynoate.

19. An insecticidal and miticidal composition comprising an acceptable carrier and as the active toxicant an insecticidally or miticidally effective amount of a compound of the formula:

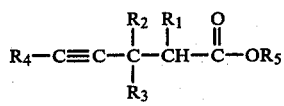

wherein:
$R_1$ is ethyl, isopropyl or cyclopropyl,
$R_2$ and $R_3$ are independently hydrogen or methyl,
$R_4$ is hydrogen, and
$R_5$ is

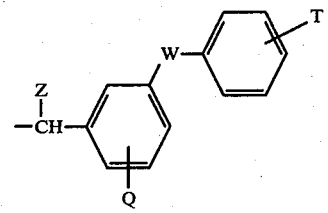

wherein:
Z is cyano,
Q and T are hydrogen, and
W is oxygen.

20. A method of controlling insects and mites which comprises subjecting them to an insecticidally or miticidally effective amount of a compound of the formula:

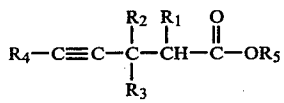

wherein:
$R_1$ is:
  an alkyl or alkenyl group having no more than five carbon atoms, or
  a cycloalkyl or cycloalkenyl group having no more than six carbon atoms;
$R_2$ and $R_3$ are independently:

hydrogen, or
an alkyl group having no more than three carbon atoms;

R₄ is:
hydrogen,
an alkyl or alkenyl group having no more than ten carbon atoms, or
phenyl or phenyl substituted with alkyl, halogen, cyano, nitro, alkoxy, alkylthio, alkylsulfinyl, alkylsulfonyl or dialkylamino groups; and R₅ is a member of the group consisting of:

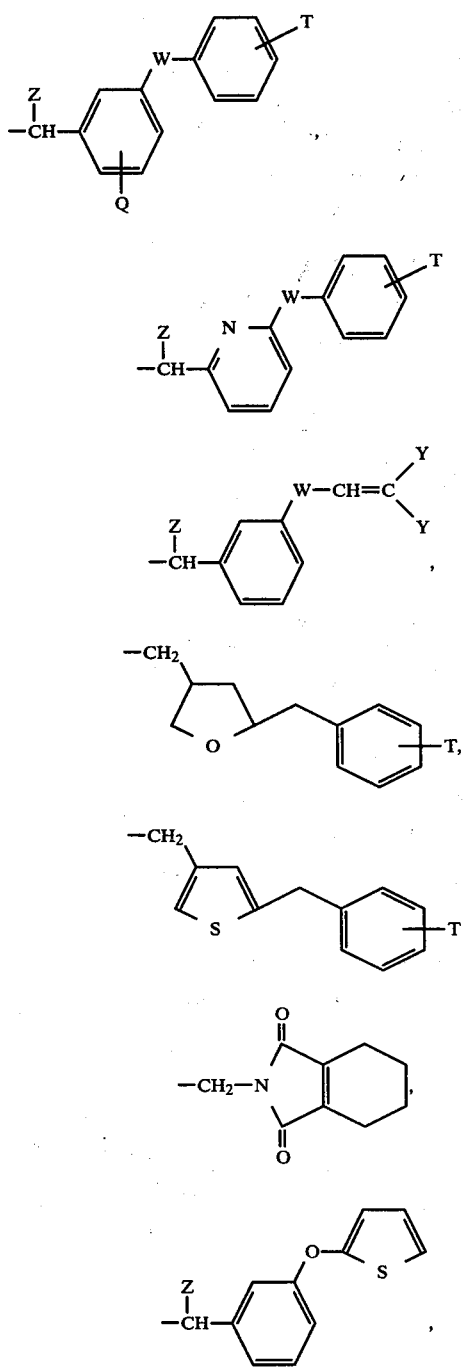

-continued

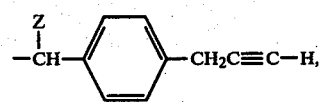

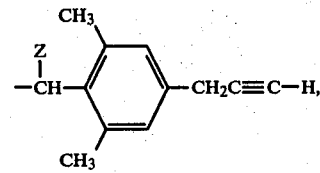

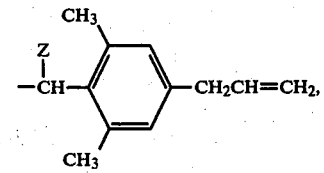

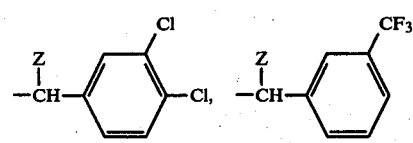

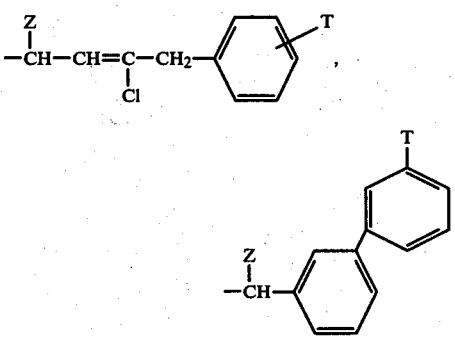

wherein:
Z is:
hydrogen,
cyano,
thioamido,
an alkyl or haloalkyl group having no more than three carbon atoms,
a cycloalkyl or cycloalkenyl group having no more than six carbon atoms, or
an alkenyl, haloalkenyl, or alkynyl group having no more than five carbon atoms;

Q and T are independently:
hydrogen,
cyano,
nitro,
halogen,
alkyl,
haloalkyl,
alkylthio,
alkylsulfinyl
alkylsulfonyl
dialkylamino,
acylamido,
alkoxy,
aryloxy,
arylthio,
arylsulfinyl, or arylsulfonyl,
provided that neither Q or T includes more than three aliphatic carbon atoms or more than six aromatic carbon atoms;

W is:
oxygen,
sulfur or its oxides, or
methylene; and

Y is:
bromine or
chlorine,

21. A method according to claim 20 wherein $R_1$ is ethyl, isopropyl or cyclopropyl.

22. A method according to claim 21 wherein $R_2$ and $R_3$ are hydrogen or when either $R_2$ or $R_3$ is hydrogen then the other member of this pair is methyl.

23. A method of controlling insects and mites which comprises subjecting them to an insecticidally or miticidally effective amount of a compound of the formula:

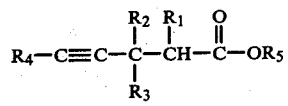

wherein:
$R_1$ is: ethyl, isopropyl or cyclopropyl;
$R_2$ and $R_3$ are hydrogen or when either $R_2$ or $R_3$ is hydrogen then the other member of this pair is methyl;
$R_4$ is:
hydrogen; and
$R_5$ is a member of the group consisting of:

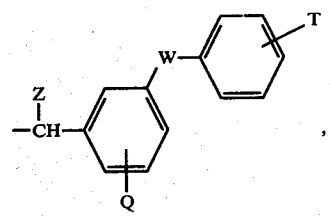

,

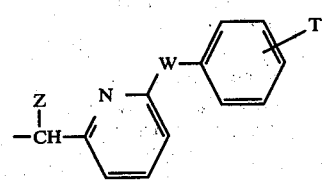

,

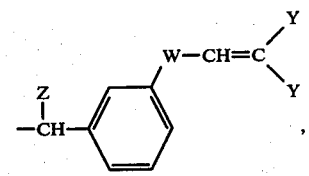

,

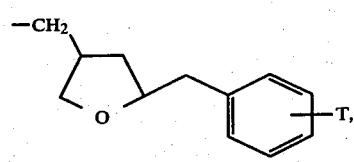

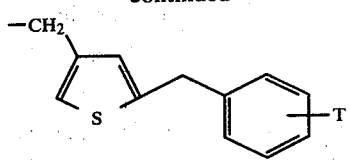

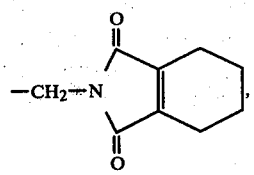

,

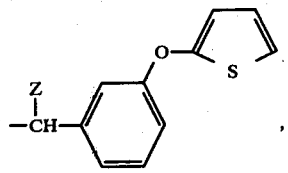

,

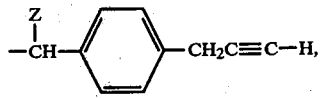

,

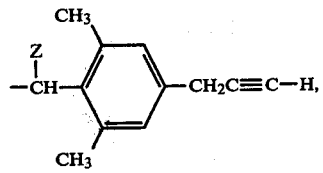

,

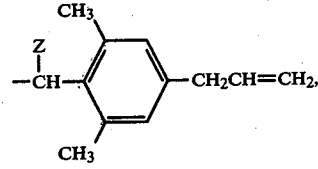

,

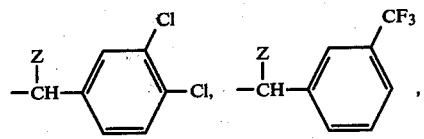

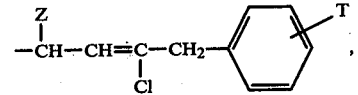

,

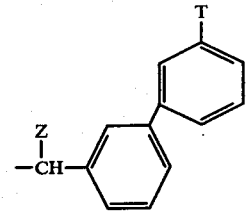

wherein:
Z is:
hydrogen,
cyano,
thioamido, an alkyl or haloalkyl group having no more than three carbon atoms, a cycloalkyl or cycloalkenyl group having no more than six carbon atoms, or an alkenyl, haloalkenyl, or alkynyl group having no more than five carbon atoms;

Q and T are independently:

hydrogen, cyano, nitro, halogen, alkyl, haloalkyl, alkylthio, alkylsulfinyl alkylsulfonyl dialkylamino, acylamido, alkoxy, aryloxy, arylthio, arylsulfinyl, or arylsulfonyl, provided that neither Q or T includes more than three aliphatic carbon atoms or more than six aromatic carbon atoms;

W is:

oxygen, sulfur or its oxides, or methylene; and

Y is:

bromine or chlorine.

24. A method according to claim 23 wherein $R_5$ is

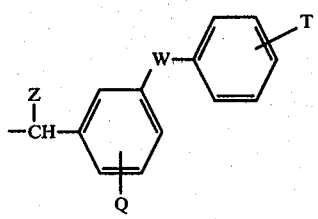

wherein:
Z is cyano,
Q and T are hydrogen, and
W is oxygen.

25. A method according to claim 23 wherein the compound is ($\alpha$-cyano-m-phenoxybenzyl) 2-isopropyl-4-pentynoate.

26. A method according to claim 23 wherein the compound is ($\alpha$-cyano-m-phenoxybenzyl) 2-isopropyl-3-methyl-4-pentynoate.

27. A method of controlling insects and mites which comprises subjecting them to an insecticidally or miticidally effective amount of a compound of the formula:

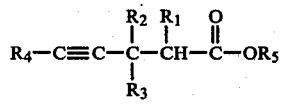

wherein:
$R_1$ is ethyl, isopropyl or cyclopropyl,
$R_2$ and $R_3$ are independently hydrogen or methyl,
$R_4$ is hydrogen, and
$R_5$ is

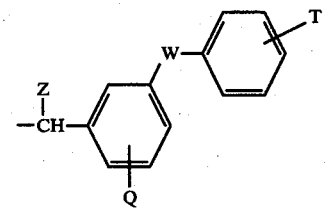

wherein:
Z is cyano,
Q and T are hydrogen, and
W is oxygen.

* * * * *